(12) United States Patent
Mahurin et al.

(10) Patent No.: US 7,217,354 B2
(45) Date of Patent: May 15, 2007

(54) METHOD AND APPARATUS FOR DETECTION OF CHEMICAL VAPORS

(75) Inventors: Shannon Mark Mahurin, Knoxville, TN (US); Sheng Dai, Knoxville, TN (US); Josip Caja, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 804 days.

(21) Appl. No.: 10/652,452

(22) Filed: Aug. 29, 2003

(65) Prior Publication Data

US 2005/0045493 A1    Mar. 3, 2005

(51) Int. Cl.
*G01N 27/22* (2006.01)

(52) U.S. Cl. .......................... 205/775; 204/400; 422/98

(58) Field of Classification Search ................ 204/400, 204/431; 205/775; 422/98; 73/31.05
See application file for complete search history.

(56) References Cited

U.S. PATENT DOCUMENTS

| | | | |
|---|---|---|---|
| 4,016,490 A | | 4/1977 | Weckenmann et al. |
| 4,878,015 A | * | 10/1989 | Schmidt et al. ............. 324/71.5 |
| 5,827,602 A | | 10/1998 | Koch et al. |
| 5,855,809 A | * | 1/1999 | Angell et al. ............... 252/62.2 |
| 5,965,054 A | | 10/1999 | McEwen et al. |
| 5,973,913 A | | 10/1999 | McEwen et al. |
| 6,033,370 A | | 3/2000 | Reinbold et al. |
| 6,212,956 B1 | | 4/2001 | Donald et al. |
| 7,060,169 B2 | * | 6/2006 | Rohrl .......................... 204/431 |

OTHER PUBLICATIONS

Kotz, R. et al., "Principles and Applications of Electrochemical Capacitors," Electrochimica Acta, 2000, 2483-2498, 45.
Hagleitner, C. et al., "Smart Single-chip Gas Sensor Microsystem," Letters to Nature, 2001, 293-296, 414.
McEwen, A. et al., "Electrochemical Properties of Imidazolium Salt . . . ," J. Electrochem. Soc., 1999, 1687-1695, 146(5).

* cited by examiner

*Primary Examiner*—Kaj K. Olsen
(74) *Attorney, Agent, or Firm*—Shelley L. Stafford; Joseph A. Marasco

(57) ABSTRACT

The present invention is a gas detector and method for using the gas detector for detecting and identifying volatile organic and/or volatile inorganic substances present in unknown vapors in an environment. The gas detector comprises a sensing means and a detecting means for detecting electrical capacitance variance of the sensing means and for further identifying the volatile organic and volatile inorganic substances. The sensing means comprises at least one sensing unit and a sensing material allocated therein the sensing unit. The sensing material is an ionic liquid which is exposed to the environment and is capable of dissolving a quantity of said volatile substance upon exposure thereto. The sensing means constitutes an electrochemical capacitor and the detecting means is in electrical communication with the sensing means.

20 Claims, 11 Drawing Sheets

METHOD AND APPARATUS FOR DETECTION OF CHEMICAL VAPORS

The United States Government has rights in this invention pursuant to contract no. DE-AC05-00OR22725 between the United States Department of Energy and UT-Battelle, LLC.

FIELD OF THE INVENTION

The present invention relates to sensing devices and methods for detecting chemicals disposed in a vapor and more particularly a non-aqueous electrochemical capacitance gas detector for detecting airborne volatile organic and/or inorganic substances.

BACKGROUND OF THE INVENTION

Detecting low concentration levels of vapors in a particular atmosphere can be critical to the health of workers, the occupants of the eco-system, or the completion of an industrial or research process. Often times, a quick, sensitive and portable gas detector is needed. In many circumstances, a gas detector or detection system capable of detecting mixtures of vapors is required.

Although a variety of methods and devices for chemical gas sensing have been developed, including cantilever-based sensors and calorimetric-based sensors, the needs have not been fully met. The existing cantilever-based and calorimetric-based gas detectors are generally bulky and difficult to make them portable without sacrificing sensitivity. The existing capacitance-based gas detectors, though less bulky, are also low in sensitivity, especially with less expensive units. The existing capacitance detectors are generally derived from the conventional dielectric capacitors with polymers as the electrolytes. When the polymer is exposed to an organic vapor/analyte, the analyte becomes physisorbed in the polymer, which changes its dielectric coefficient, and in turn, alters the capacitance of the detector and signals the presence of an analyte. Polymer-based dielectric capacitors have been developed that are quite small (on the order of a few hundred microns) and which use interdigitated electrodes separated by 1–2 µm with a polymer layer of approximately 5 µm. At this size, these capacitors generally exhibit nominal capacitance values in the pico-farad range. Furthermore, since the capacitance variances are triggered by changes in the dielectric coefficient of a polymer upon absorption of volatile organic compounds, these variances are expected to be small and typically fall in the attofarad range. Consequently, the dielectric capacitance detectors require sophisticated, highly sensitive and expensive measuring devices to measure these small capacitance variances. In addition to the necessity for sophisticated measuring devices, the small capacitance variances can essentially impose a constraint on the detection limit of the device. Polymer-based capacitive sensors that have a detection limit of approximately 5 ppm for ethyl alcohol have been reported in the literature. The existing dielectric capacitance-based gas detectors further suffer from a slow analyte diffusion rate through the conductive polymer, which prolongs the chemical detection response and the recovery process.

Therefore, a need exists for a gas detector that can quickly and reliably detect a change in capacitance caused by an analyte contacting a sensing material, and further needed, is a gas detector or detection system that can detect the presence of and analyze the concentrations of multiple vapors in an environment, particularly hazardous vapors.

OBJECTS OF THE INVENTION

Accordingly, objects of the present invention include a new and improved method and device for detecting volatile organic and/or inorganic substances in a quick, easy and reliable system.

It is a further object of the present invention to provide a new detection system capable of detecting and analyzing the presence of multiple vapors in an environment.

Further objects of the present invention will become apparent from the description contained herein.

SUMMARY OF THE INVENTION

In accordance with one aspect of the present invention, the foregoing and other objects are achieved by a gas detector for detecting and identifying volatile organic and/or volatile inorganic substances present in vapors in an environment. The gas detector comprises a sensing means and a detecting means for detecting electrical capacitance variance of the sensing means and for further identifying volatile organic and/or volatile inorganic substances. The sensing means comprises at least one sensing unit and a sensing material allocated therein the sensing unit, the sensing material is an ionic liquid which is exposed to the environment and is capable of dissolving a quantity of the volatile substance upon exposure thereto. The sensing means constitutes an electrochemical capacitor and the detecting means is in electrical communication with the sensing means.

A method for detecting and identifying volatile organic and/or volatile inorganic substances present in vapors in an environment comprising the steps of first, providing a gas detector having a sensing means and a detecting means for detecting electrical capacitance variance of the sensing means and for further identifying the volatile organic and/or volatile inorganic substances, the sensing means comprises at least one sensing unit having a sensing material allocated therein and the sensing material being an ionic liquid which is exposed to the environment and is capable of dissolving a quantity of the volatile substance upon exposure thereto. The sensing means constitutes an electrochemical capacitor and the detecting means is in electrical communication with the sensing means. The sensing unit further comprises an electrically nonconductive housing having the ionic liquid allocated therein and the housing having a recessed area or opening for allowing the ionic liquid to be exposed to the environment and is capable of dissolving a quantity of said volatile substance upon exposure thereto, the sensing unit further comprises a plurality of electrodes within close proximity of one another disposed within the housing. The plurality of electrodes is in electrical communication with the ionic liquid and the plurality of electrodes further being coated with the ionic liquid. The detecting means comprises at least one capacitance detection circuit in electrical communication with the sensing unit and a means to analyze and display data obtained by the capacitance detection circuit. Then, the gas detector is placed in the environment that is to be analyzed and the ionic liquid is exposed to said environment for a sufficient time to allow a quantity of the volatile substance to dissolve in the ionic liquid and to allow the ionic liquid to adsorb onto the surface of the electrodes, thereby altering the capacitance of the electrochemical capacitor wherein the ionic liquid is an electrolyte.

BRIEF DESCRIPTION OF THE DRAWINGS

FIG. 3b is a top view of the embodiment of FIG. 3a.

FIG. 4b is a top view of the embodiment of FIG. 4a.

For a better understanding of the present invention, together with other and further objects, advantages and capabilities thereof, reference is made to the following disclosure and appended claims in connection with the above-described drawings.

DETAILED DESCRIPTION OF THE INVENTION

The present invention is a non-aqueous electrochemical capacitance-based gas detector for detecting airborne volatile organic or inorganic compounds and substances. The apparatus of the present invention is based on observations that when an ionic liquid is exposed to an environment containing a volatile substance, the ionic liquid dissolves a quantity of the volatile substance and then adsorbs on the surface of carbon electrodes, thereby altering the capacitance of the electrochemical capacitor where the ionic liquid is the electrolyte. In addition, different volatile substances alter the capacitance of the electrochemical capacitor in unique ways when dissolved in the ionic liquid. Similarly, different concentrations of a particular volatile substance also uniquely alter the capacitance of a particular electrochemical capacitor. The capacitance-based gas detector of the present invention taught and claimed herein, therefore, exhibits a capability of detecting volatile organic and inorganic substances both qualitatively and quantitatively.

Figure 1:
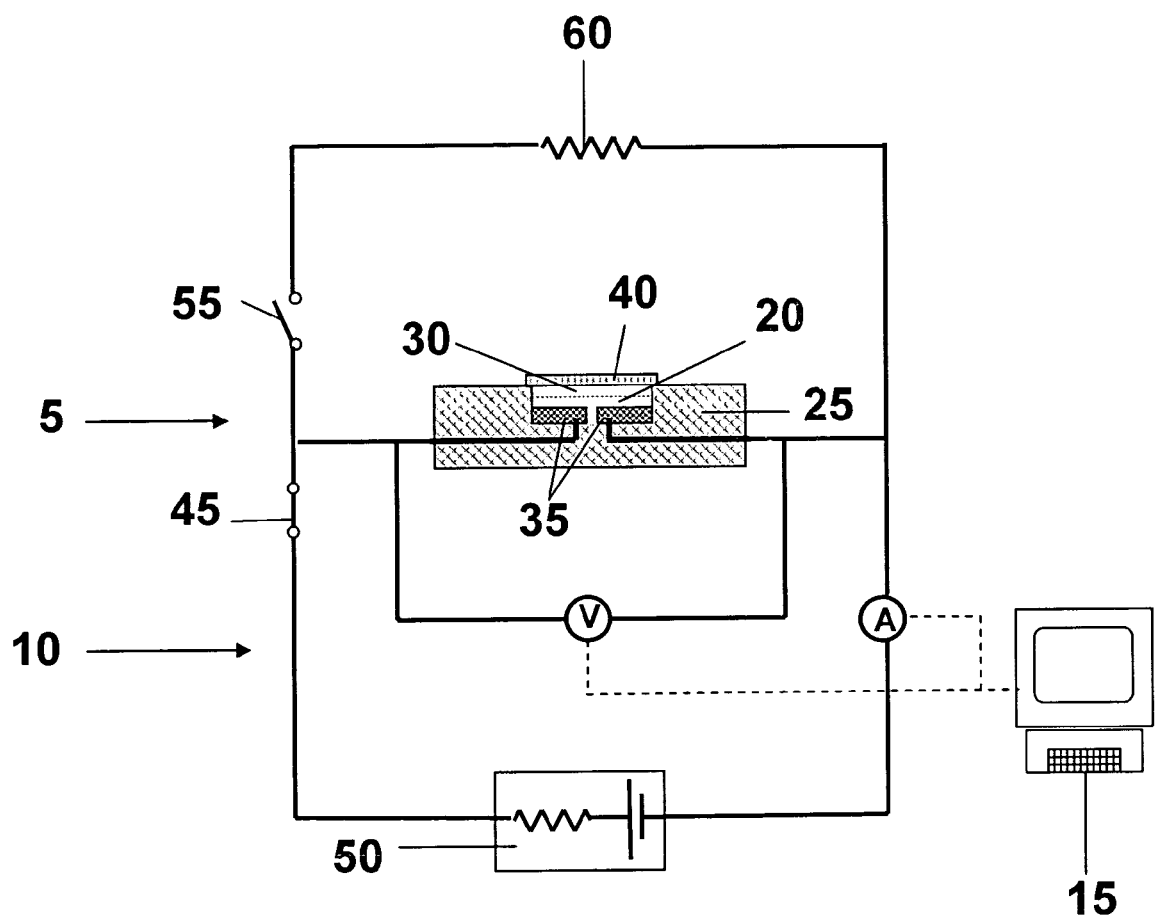
FIG. 1 is a schematic representation of a capacitance-based gas detector of the present invention capable of detecting volatile organic and volatile inorganic compounds and substances both qualitatively and quantitatively.

FIG. 1 is a schematic representation of the non-aqueous electrochemical capacitance-based gas detector of the present invention which comprises two primary elements: a sensing means and a detection means for detecting the capacitance variance of the sensing means. The sensing means and the detection means are in electronic communication with each other. The sensing means comprises at least one sensing unit 5 and a sensing material which is an ionic liquid 20, disposed within the sensing unit and wherein the ionic liquid 20 is further exposed to the environment being detected. The sensing means which comprises the sensing unit S with the sensing material 20 constitutes an open-form electrochemical capacitor. The sensing unit 5 further comprises an electrically nonconductive housing 25 having a recessed area or an opening 30 and a plurality of electrodes 35 disposed in the housing 25, separated from each other and in electrical communication with each other through the ionic liquid 20. The sensing unit 5 may further have a membrane 40 covering the opening 30 to enclose the ionic liquid. The membrane 40 must be electrically insulating and it must allow free penetration of airborne compounds. In addition, the membrane material must be chemically compatible, i.e., inert, with the ionic liquid. While the membrane 40 allows airborne compounds from an environment to contact the ionic liquid 20, the membrane 40 does not allow the ionic liquid 20 to disperse to the environment.

The detection means disclosed comprises at least one capacitance detection circuit 10 and a device 15 programmed to analyze and display the data obtained by the detection circuit 10. For example, in Example 1, a Vernier Labpro multimeter 12 attached to a personal computer with LoggerPro software installed was used to measure and display the data obtained by the detection circuit. In FIG. 1, the capacitance detection circuit measures the capacitance wherein switch 1 (45) is closed and the capacitor (sensing unit 5) is charged at a constant current, as indicated on the ammeter A, by the power supply 50. At the same time, the voltage across the capacitor is measured using a voltmeter V which can be directly connected to a computer 15 to display the voltage as a function of time. The capacitance is then given by: $C=(I\Delta t)/\Delta V$. When the charge is completed, Switch 1 (45) is opened while Switch 2 (55) is closed to allow the capacitor to discharge through a resistor 60. Once discharged, the capacitor is ready for the next measurement. Measurement of the capacitance can also be done on the discharge cycle instead of the charge cycle.

Figure 2:
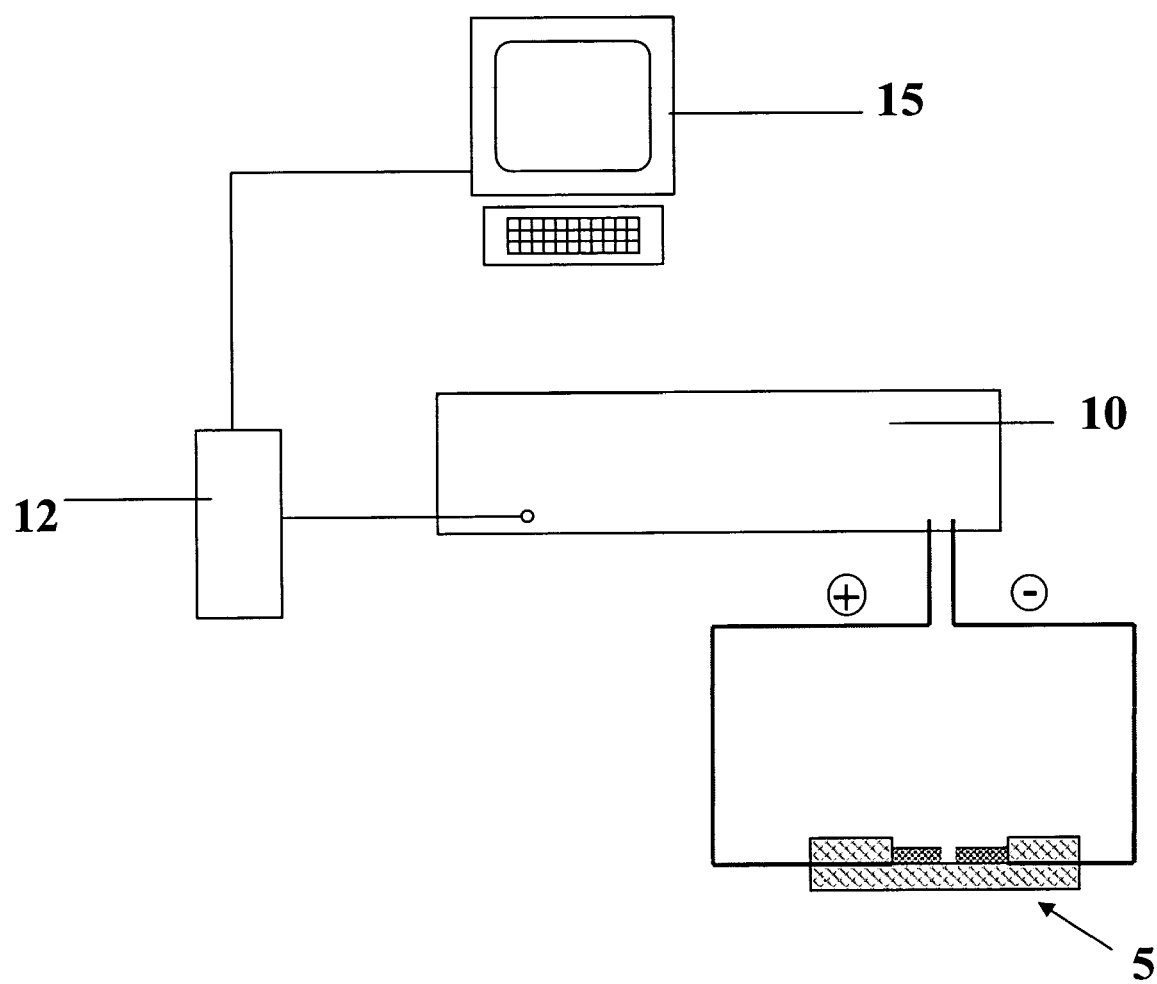
FIG. 2 is a schematic diagram of the capacitance-based gas detector of the present invention wherein the power supply, ammeter, voltmeter and load resistance are all in one unit.

FIG. 2 shows another embodiment of the present invention wherein the power supply, ammeter, voltmeter and load resistance are all in one unit, such as an EG&G Model 263A Potentiostat/Galvanostat as used in Example 1.

Figure 3A:
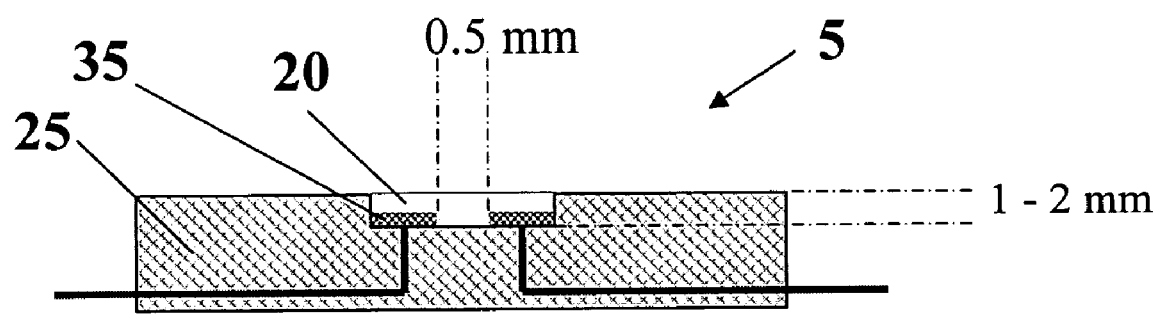
FIG. 3a is a cross sectional view of one embodiment of the sensing unit of the capacitance-based gas detector of the present invention, wherein the electrodes and ionic liquid are disposed within the recessed area of the nonconductive housing.

The sensing unit 5 can use a variety of configurations to form an electrochemical capacitor having substantially similar performance characteristics. The housing 25 may be unitary, i.e., one piece, or comprised of various components or elements, i.e., multi-piece. The material used for the housing 25 is electrically nonconductive and sufficiently contains the ionic liquid 20, maintaining electrical communication between the ionic liquid and the electrodes. In one embodiment, as shown in FIG. 3a and also in FIG. 1, the ionic liquid 20 and the electrodes 35 are disposed in the recessed area 30 of a unitary housing 25 which is made of a nonconductive material. Nonconductive materials that may be used for the housing 25 for the different embodiments of the present invention include polymers such as polypropylene, Teflon and polyethylene. Other nonconductive materials that may also be used include alumina and glass.

The electrodes 35 used with the different embodiments of the present invention may be fashioned in various geometric shapes and sizes, for example, circles or squares, and placed in various configurations. However, the electrodes are preferred to be thin and must be placed within a close proximity to each other so to promote electrical communication through the ionic liquid 20. In the embodiment illustrated in FIG. 1 and FIG. 3a, the side-by-side electrodes are circular with a diameter of 3–5 mm, approximately 0.13 mm in thickness, and less than 1–2 mm apart. In another embodiment illustrated in FIG. 4a, FIG. 4b and FIG. 4c, the electrodes are placed in a concentric configuration and approximately 1 or 1.5 mm apart. The optimal separation between the electrodes is less than 1 mm.

Figure 3B:
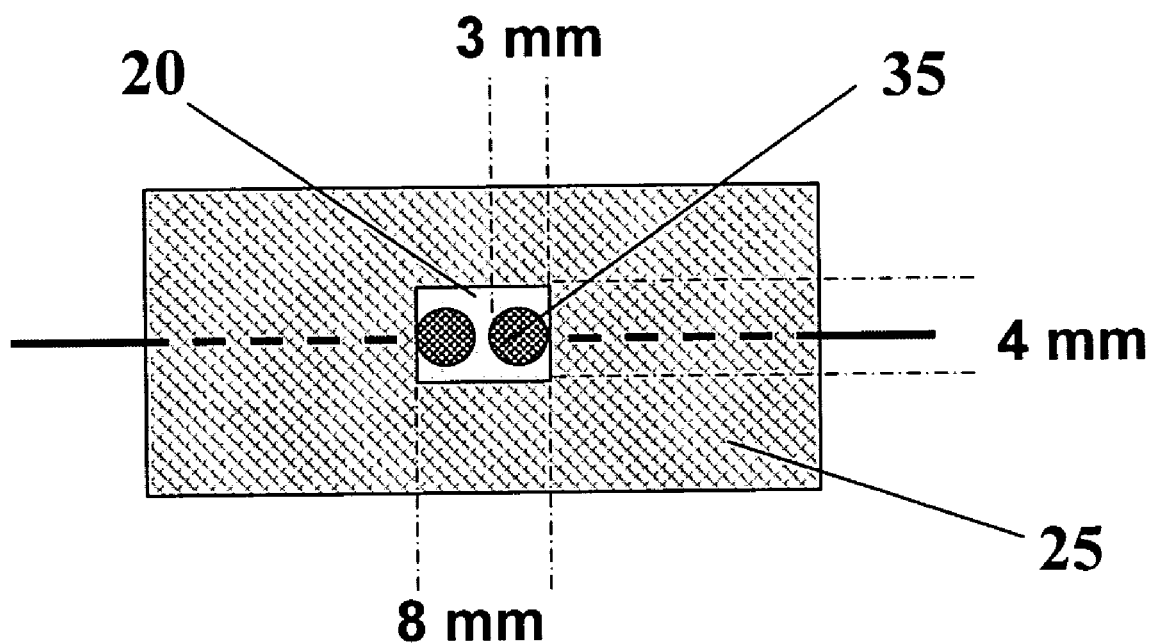

The electrodes 35 are generally made of electrically conductive and chemically resistive high surface area materials, such as activated carbon, carbon nanotubes or porous metal oxides, such as tin oxide. The preferred material is activated carbon since it is a porous material that typically has a high surface area (sometimes as high as 3000 m²/g.). For example, carbon electrode material PACMM100, manufactured by Material Methods, LLC, Newport Beach, Calif., was used in the embodiments shown in the figures and discussed in the Examples below. Activated carbon is also electrically conductive and generally inert when exposed to a wide variety of chemical reactions. The electrodes used with the embodiments of the present invention were glued to a thin copper foil, which serves as a current collector. FIG. 3b shows a top view of the embodiment of FIG. 3a.

Figure 3C:
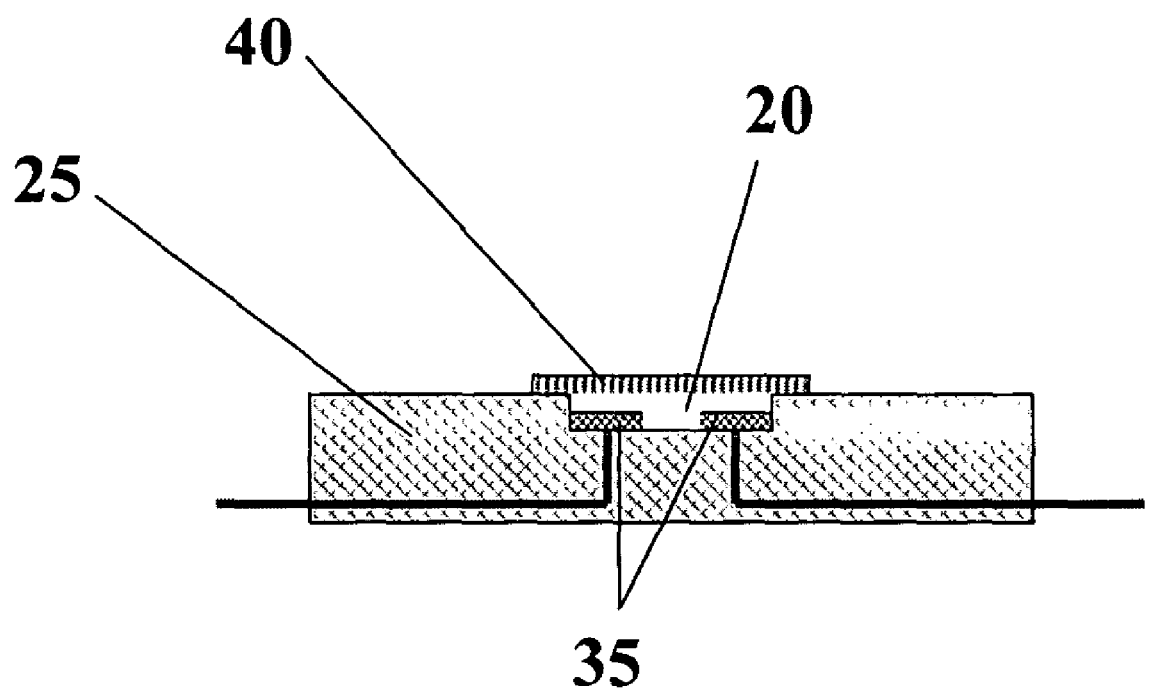
FIG. 3c is a cross sectional view of the sensing unit of the capacitance-based gas detector wherein a membrane covers the opening of the recessed area of the nonconductive housing.

Another embodiment of the present invention is illustrated in FIG. 3c wherein a membrane 40, as also shown in FIG. 1, is used to cover the recessed area or opening 30 of the housing 25. The membrane material must be electrically insulating and it must allow free penetration of airborne compounds. In addition, the membrane material must be chemically compatible, i.e., inert, with the ionic liquid. For general vapor detection works, the preferred membrane has pore dimensions that allow the analyte to pass through with little or no reduction in the detection time. Alternatively, the membrane can be made selective if it has appropriate pore dimensions or the pore surfaces have been chemically modified to prevent the diffusion of all vapors except the one of interest. The membrane used in Example 1 below is Celgard 2500 (Hoechst-Celanese) thickness 0.025 mm. While the membrane 40 allows airborne compounds from an environment to contact the ionic liquid 20, the membrane 40 does not allow the ionic liquid 20 to disperse to the environment. The membrane 40 therefore further serves to contain the ionic liquid 20.

Figure 4A:
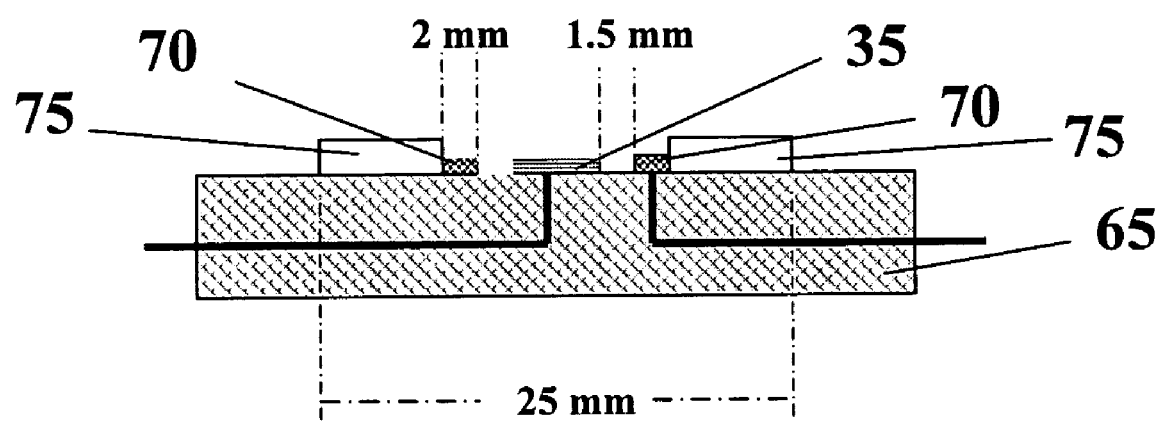
FIG. 4a is a cross sectional view of a second embodiment of the sensing unit of the capacitance-based gas detector of the present invention, wherein concentric electrodes and the ionic liquid are positioned on top of a nonconductive base and contained by another nonconductive material as a side wall.
Figure 4B:
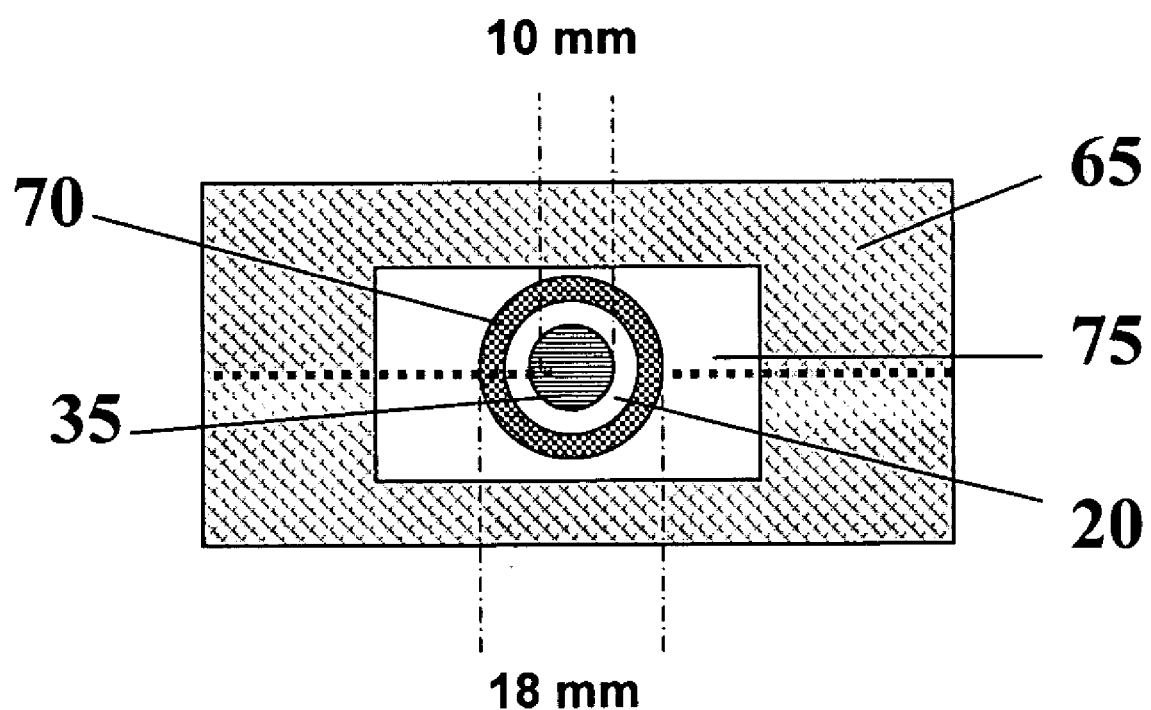
Figure 4C:
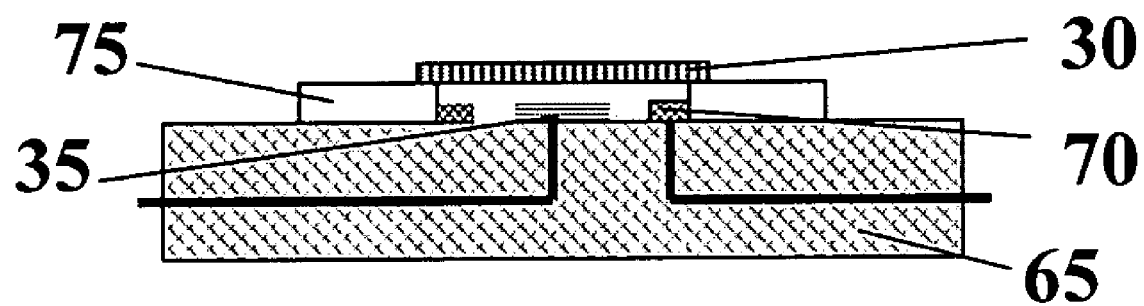
FIG. 4c is a cross sectional view of the embodiment of FIG. 4a wherein a membrane covers the opening.

In another embodiment, shown in FIG. 4a and top view shown in FIG. 4b, the electrodes 35 and 70 are in a concentric configuration wherein one electrode 35 is in the center and surrounded by a second electrode 70, placed 1.5 mm apart and each having a diameter of 2 mm. The ionic liquid 20 and the electrodes 35 and 70 are disposed on a base 65 made of a nonconductive material, such as plastic, and contained by a nonconductive side wall component 75. The nonconductive side wall component 75 may be a separate component to the base or it could be a unitary piece with the base as shown in FIGS. 1, 2, 3a, 3b and 3c. In FIGS. 4a, 4b and 4c, the side wall component separate component to the base wherein the side wall component is adhered to the base or attached to the base by a permanent means. A better view of this concentric configuration can be seen from the top view in FIG. 4b. FIG. 4c illustrates the electrochemical capacitor device of FIGS. 4a and 4b further having a membrane 30 covering the electrodes 35, 70 and ionic fluid 20 thereby providing a means to allow airborne substances from an environment to contact the ionic liquid 20, while not allowing the ionic liquid 20 to disperse to the environment.

The ionic liquid 20 disposed in the electrochemical gas detector of the present invention can be composed of a cation selected from the group consisting of,

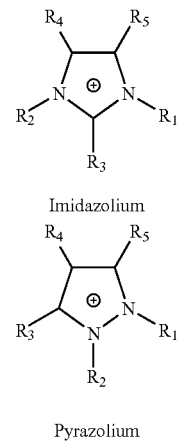

Imidazolium

Pyrazolium wherein $R_1$ and $R_2$ represent, independently, an alkyl group comprising 1 to 12 carbon atoms, and $R_3$, $R_4$, and $R_5$ represent either H, F, or separate alkyl groups of 1 to 5 carbon atoms, and an anion selected from the group consisting of $PF_6^-$, $BF_4^-$, $AsF_6^-$, triflate, imide, BETI, and imide ion of the type $(FX^1O)N^{-(OX^2}F)$ wherein $X^1$ and $X^2$ are the same or different and comprise SO or PF. It is important to maintain a thin and homogeneous layer of ionic liquid over the electrodes. The ionic liquid must substantially cover the electrode surface area and provide electrical communication between the electrodes. The analyte diffusion time and the device detection time increase as the depth of the ionic liquid increases. The depths of ionic liquid layers are preferred to be less than 1 mm thick.

One of the benefits of using ionic liquids instead of polymers, as used in the dielectric capacitance-based gas detectors, is improved sensitivity. When an ionic liquid is exposed to an organic volatile substance, this substance dissolves in the ionic liquid and adsorbs on the surface of the electrodes and alters the electrical double layer of the electrodes, consequently, causing changes in the capacitance of the sensing unit (capacitor). Since the capacitors with ionic liquids generally achieve much higher capacitance than the ones with polymers, the capacitance variances caused by the changes in ionic liquids' physical and electrical properties are generally larger than the capacitance variances caused by the property-change of the polymers. Thus, the inventive gas detectors with ionic liquids can achieve higher sensitivity than the dielectric capacitance-based gas detectors with polymer while using less sophisticated and less expensive measuring devices. Another benefit of using ionic liquids over polymers is the shortened detection time and recovery time because the diffusion rates of organic volatile substances through an ionic liquid are generally faster than through a polymer sensing material.

A particular ionic liquid may change its physical and electrical properties significantly when exposed to an organic substance, but to another organic substance, may respond only with minor alteration. Thus, a sensing unit can be tuned to detect specific volatile organic substances by selecting an analyte-specific ionic liquid. Furthermore, an array of analyte-specific sensing units, each connected with its detection means, or a detection circuit within the detection means, can build the inventive gas detector or system for multiple organic vapor detections.

The capacitance detection circuit 10 in an inventive gas detector or system may employ any conventional capacitance detection circuits/devices. For example, in one embodiment illustrated in FIG. 1, the detection circuit 10 includes a power supply such as a Hewlett-Packard low voltage power supply, a means to measure voltage and current such as a Fluke 180 digital multimeter, a load resistance 50, and a means to switch back and forth between the charge cycle and discharge cycle (switches 45, 55). In another embodiment illustrated in FIG. 2, the detection circuit is a EG&G Potentiostat/Galvanostat (Model 263A) unit used for the constant current charge-discharge measurement of capacitance.

Any conventional capacitance measuring method can be employed. For example, the capacitance of a particular sensing unit can be measured during a discharge cycle after the sensing unit is first charged to an initial voltage less than two volts. During the discharge cycle, the voltage is measured at discrete time intervals and the values are stored for analysis. The initial and final voltages as well as the time and current are then used to obtain the capacitance from the following equation: $C = I\Delta t/\Delta V$. The capacitance measurement can be performed on the charge cycle in a similar manner using analogous measurement points.

The data points can also be submitted to a programmed computer 15, at discrete time intervals, typically 0.1 sec, for display. For example, the LoggerPro software provides a straightforward method of viewing and analyzing the complete charge-discharge curve. In principle, however, it is not necessary to use the complete curve. The capacitance can be calculated by noting the initial and final voltages, the constant current, and the time. This can be accomplished completely within an electronic circuit with only the final capacitance being displayed.

Furthermore, by testing the capacitance variances of a particular organic volatile substance at different concentrations, a concentration curve of the analyte corresponding to a particular ionic liquid can be drawn. In turn, a concentration data bank can be established for multiple organic vapors with one ionic liquid. An array data series can also be collected for different ionic liquids. The data banks and array date can provide fingerprint maps and/or concentration curves for field chemical detection and analysis techniques, which make the qualitative and quantitative gas detection possible.

The inventive gas detector/system can be used in industrial settings, research labs, and natural environment by placing the sensing unit 5 or array of sensing units in the environment and periodically measuring the capacitances of the sensing unit(s). Then, the data points can be analyzed and compared with the background/blank data and the data banks.

Having described the invention, the following examples are given to illustrate specific applications of the invention including the best mode now known to perform the invention. These specific examples are not intended to limit the scope of the invention described in this application.

EXAMPLE 1

Figure 5A:
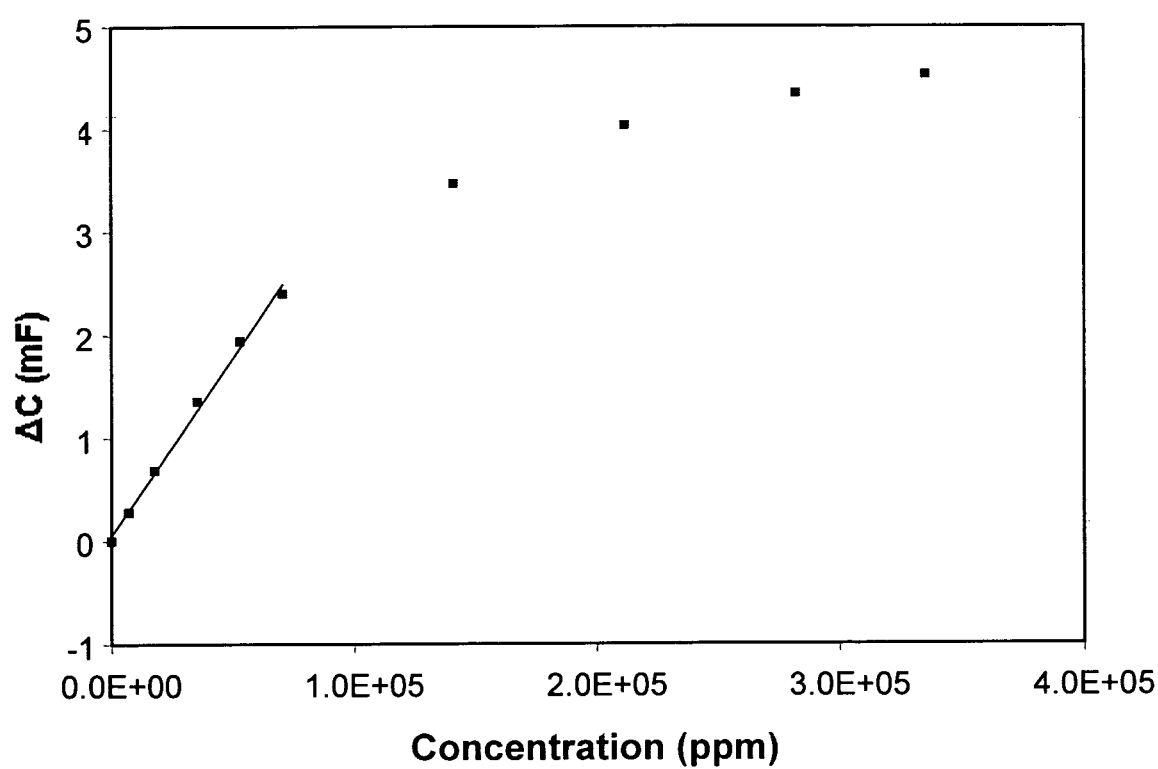
FIG. 5a shows the calibration curve of acetone using $N_2$ as a carrier gas.
Figure 5B:
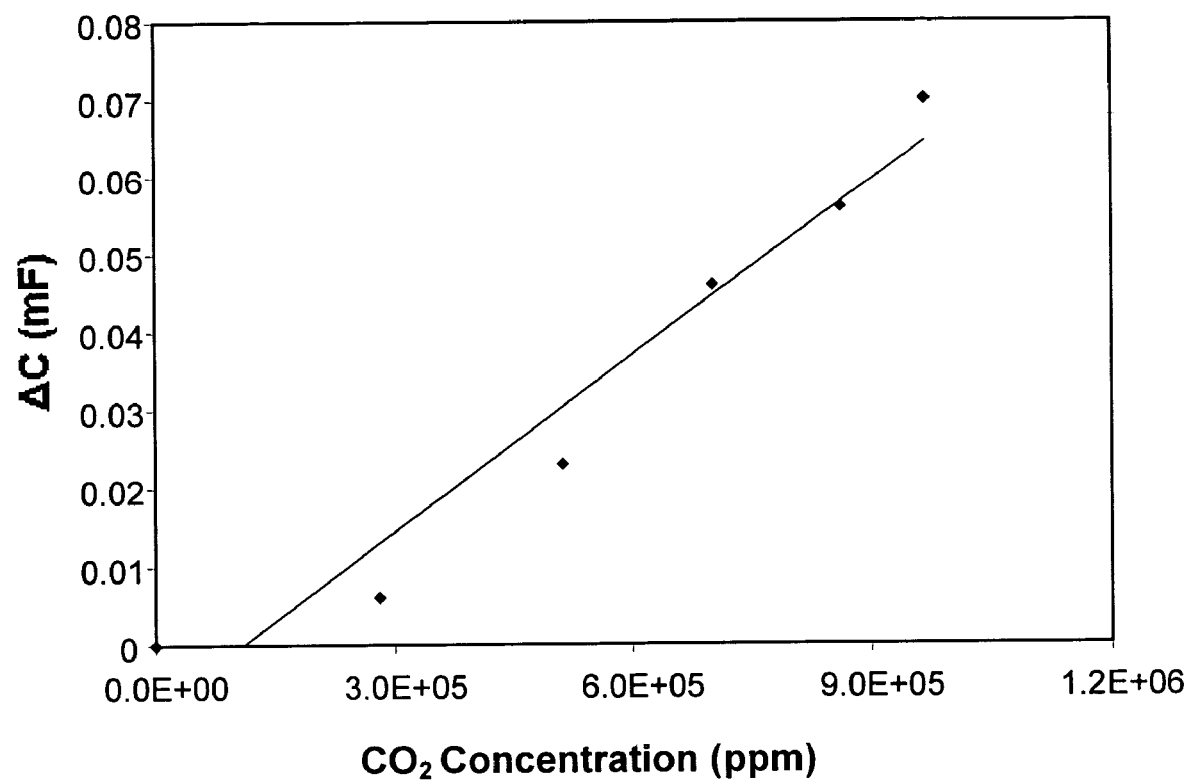
FIG. 5b shows the calibration curve of $CO_2$ using $N_2$ as a carrier gas.

In order to test the sensitivity of the invention, a calibration curve for acetone vapor, shown in FIG. 5a and carbon dioxide, FIG. 5b, were measured using the embodiment given in FIG. 5a and FIG. 5b with approximately 4 mg of the ionic liquid 1-ethyl-3-methylimidazolium bis(trifluoromethylsulfonyl)imide, which produced a layer of 0.5 mm thickness. The gas detector system was placed in a 500 mL enclosed container with electrical leads to the outside of the container for capacitance measurements as well as flow ports connected to a gas flow system for the introduction of the organic or inorganic vapor. A stream of saturated vapor was first obtained by bubbling dry, high-purity nitrogen through a liquid reservoir such as acetone. Dilution of the saturated vapor stream was achieved by mixing the saturated vapor with a second stream of dry nitrogen. The flow rates of the saturated vapor stream and the dry nitrogen stream were independently controlled by mass flow controllers (MKS Instruments). The ratio of the flow rates of the two streams determined the final concentration of the organic vapor. In order to eliminate artifacts that might occur as a result of differences in flow rate, the total flow rate was maintained at a constant value of 1000 sccm (standard cubic centimeters per minute) as the ratio of the two streams, hence the acetone concentration, was varied. The system was operated at a constant temperature of 25° C.

Prior to measuring the acetone calibration curve, the container with the capacitive gas detector was purged with a steady flow of dry nitrogen at a flow rate of 1000 sccm for 10 minutes. This served to remove water vapor from the ionic liquid and produce an equilibrium capacitive baseline for the gas detector. To obtain the first point in the acetone calibration curve in FIG. 5a, an analyte containing stream that consisted of a 2% saturated vapor stream in dry nitrogen (achieved by flowing 20 sccm saturated acetone vapor with 980 sccm dry nitrogen to produce a ratio of 2%) was flowed through the cell. The acetone concentration of this particular vapor stream was determined to be approximately 7000 ppm. The diluted acetone vapor stream was flowed through the cell for approximately 1 minute and the capacitance was measured and recorded using an EG&G Potentiostat/Galvanostat (Model 263A) connected to a personal computer as shown in the embodiment in FIG. 2. Once the first point on the calibration curve was measured, dry nitrogen was again flowed through the system in order to purge the cell of any residual acetone and return the capacitor to its baseline value. The calibration curves shown in FIG. 5a was then constructed by measuring the capacitance of the detector at various concentrations of acetone vapor by increasing the flow rate of the acetone-saturated stream while maintaining a constant total flow rate of 1000 sccm. The sensitivity of the system to acetone vapor can be calculated from the slope of the calibration curve. From FIG. 5a, the gas detection system exhibits a sensitivity of 30 nF/ppm to acetone vapor. Capacitance variances as low as 0.1 nF are easily measured with relatively simple electronics, in contrast to the attofarad capacitance variances measured using the polymer based capacitive sensor. Thus, the inventive gas detection system described here has a nominal detection limit that is in the ppb range, which is a significant improvement over polymer based dielectric systems.

The gas detection system is not limited to organic vapors. The sensitivity of the system to carbon dioxide was measured using the same procedure outlined for acetone. The calibration curve is given in FIG. 5b. FIG. 5b gives a better view of the sensitivity of the system to the carbon dioxide analyte. Clearly, the system is less sensitive to carbon dioxide than to acetone. From the slope of the $CO_2$ calibration curve, the sensitivity to carbon dioxide is calculated to be 0.09 nF/ppm. This leads to a nominal detection limit of approximately 1 ppm.

EXAMPLE 2

Figure 6:
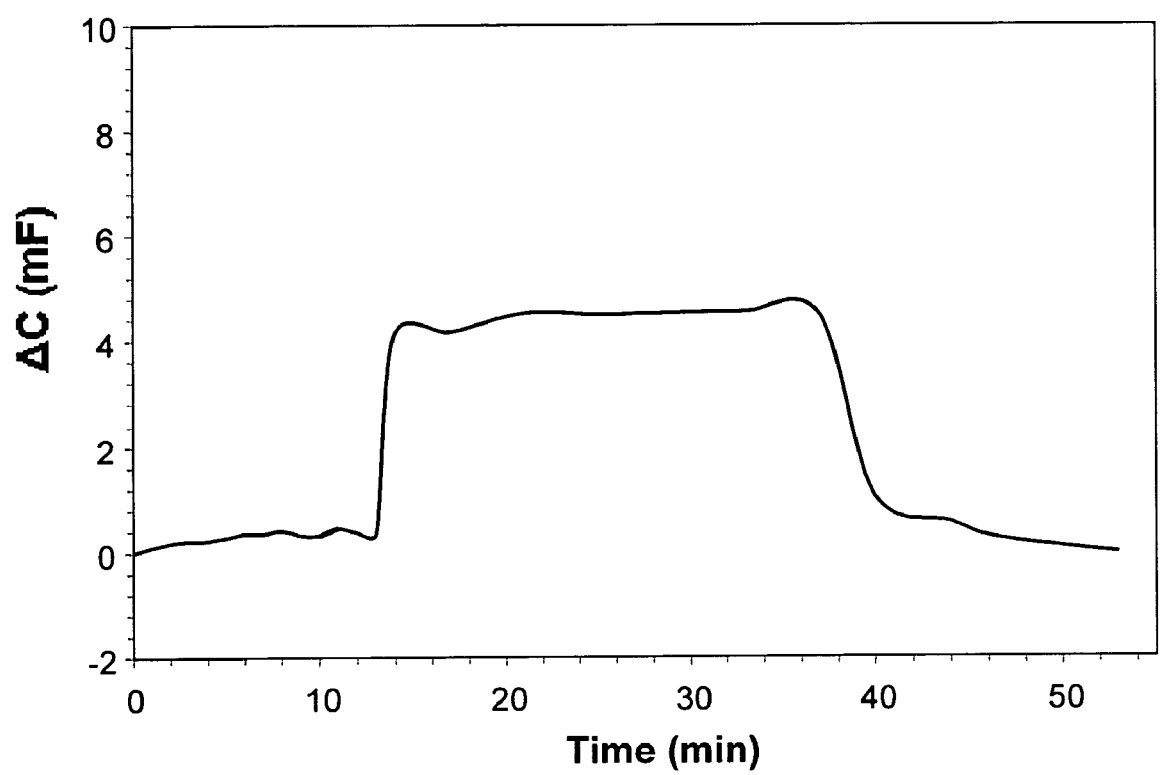
FIG. 6 shows the response of the capacitor to acetone.

The response time of the system was measured using the same container as described in Example 1 with the exception that the flow ports were closed. For the determination of the response time, measurement of the capacitance of the inventive gas detection system was first obtained at ambient conditions, i.e., without the addition of any analyte. Twenty microliters of acetone was subsequently deposited into the container, which was immediately closed to prevent leakage of the acetone. The concentration of acetone in the container after complete evaporation was calculated to be approximately 15200 ppm. The capacitance was then measured as a function of time to obtain the response of the system (see FIG. 6). As can be seen, the response time of the system was on the order of a few seconds. It should be pointed out that the capacitor utilized in this measurement employed a layer of ionic liquid of approximately 1 mm in thickness. Since the response time of the capacitor is dependent on diffusion of the analyte through the ionic liquid, thicker ionic liquid layers lead to longer response times. Thus, decreasing the thickness of the ionic liquid layer significantly reduces the response time. With careful construction, the thickness of the ionic liquid layer can be reduced to the micron scale (compare the thickness of the polymer layers in the polymer based dielectric capacitive sensors which are as low as 5 μm) which would decrease the response time to milliseconds. Diffusion of analytes through a liquid is much faster than through a solid polymer. Consequently, given similar layer thicknesses, the response time of the ionic liquid based capacitor is shorter than the response time of the polymer based capacitor.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A gas detector for detecting and identifying volatile organic and/or volatile inorganic substances present in vapors in an environment, said gas detector comprising a sensing means and a detecting means for detecting electrical capacitance variance of said sensing means and for further identifying said volatile organic and volatile inorganic substances, said sensing means comprising at least one sensing unit and a sensing material allocated therein said sensing unit, said sensing material being an ionic liquid which is exposed to said environment and is capable of dissolving a quantity of said volatile substance upon exposure thereto, said sensing means constituting an electrochemical capacitor, and said detecting means being in electrical communication with said sensing means.

2. The gas detector of claim 1 wherein said sensing unit further comprises:
   a. an electrically nonconductive housing having said ionic liquid allocated therein and said housing having a recessed area or opening for allowing said ionic liquid to be exposed to said environment; and
   b. a plurality of electrodes within close proximity of one another disposed within said housing, said plurality of electrodes in electrical communication with said ionic liquid, said plurality of electrodes further being coated with said ionic liquid.

3. The gas detector of claim 2 wherein said housing further comprises a separation means covering said recessed area or opening wherein said membrane enables said vapor to penetrate through said membrane while preventing said ionic liquid from leaking out of said housing.

4. The gas detector of claim 3 wherein said separation means is a membrane.

5. The gas detector of claim 1 wherein said detecting means comprises:
   a. at least one capacitance detection circuit in electrical communication with said sensing unit; and
   b. a means to analyze and display data obtained by said capacitance detection circuit.

6. The gas detector of claim 1 further comprising an array of sensing units wherein each sensing unit in said array has an analyte-specific ionic liquid different from the other sensing units and each sensing unit having independent electrical communication with said detecting means.

7. The gas detector of claim 1 wherein said electrodes are comprised of electrically conductive material selected from the group consisting of activated carbon, carbon nanotubes, buckyballs and porous metal oxides.

8. The gas detector of claim 1 wherein said ionic liquid has zero vapor pressure at ambient temperature.

9. The gas detector of claim 8 wherein said ionic liquid is selected from the group of ionic liquids consisting of a cation,

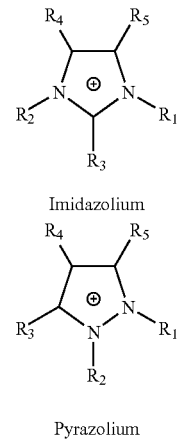

Imidazolium

Pyrazolium wherein $R_1$ and $R_2$ represent, independently, an alkyl group comprising 1 to 12 carbon atoms, and $R_3$, $R_4$, and $R_5$ represent either H, F, or separate alkyl groups of 1 to 5 carbon atoms, respectively, and said ionic liquid is selected from the group of ionic liquids consisting of an anion selected from the group consisting of $PF_6^-$, $BF_4^-$, $AsF_6^-$, triflate, imide, BETI, and imide ion of the type $(FX^1O)N^-(OX^2F)$ wherein $X^1$ and $X^2$ are the same or different and comprise SO or PF.

10. A method for detecting and identifying volatile organic and/or volatile inorganic substances present in vapors in an environment comprising the steps of:
   a. providing a gas detector having a sensing means and a detecting means for detecting electrical capacitance variance of said sensing means and for further identifying said volatile organic and/or volatile inorganic substances, said sensing means comprising at least one sensing unit and a sensing material allocated therein said sensing unit, said sensing material being an ionic liquid which is exposed to said environment and is capable of dissolving a quantity of said volatile substance upon exposure thereto, said sensing means constituting an electrochemical capacitor, and said detecting means being in electrical communication with said sensing means, said sensing unit further comprising an electrically nonconductive housing having said ionic liquid allocated therein and said housing having a recessed area or opening for allowing said ionic liquid to be exposed to said environment and is capable of dissolving a quantity of said volatile substance upon exposure thereto, said sensing unit further comprising a plurality of electrodes within close proximity of one another disposed within said housing, said plurality of electrodes in electrical communication with said ionic liquid and said plurality of electrodes further being coated with said ionic liquid, said detecting means comprising at least one capacitance detection circuit in electrical communication with said sensing unit and a means to analyze and display data obtained by said capacitance detection circuit;

b. placing said gas detector in said environment that is to be analyzed; and c. exposing said ionic liquid to said environment for a sufficient time to allow said quantity of said volatile substance to dissolve in said ionic liquid and to allow said ionic liquid to adsorb onto the surface of said electrodes, thereby altering the capacitance of said electrochemical capacitor wherein said ionic liquid is an electrolyte.

11. The method of claim 10 further comprising the step of measuring said capacitance variance of said sensing means.

12. The method of claim 11 further comprising the step of identifying said volatile substance present in said environment.

13. The method of claim 10 wherein said electrodes are comprised of electrically conductive material selected from the group consisting of activated carbon, carbon nanotubes, buckyballs and porous metal oxides.

14. The method of claim 10 wherein said ionic liquid has zero vapor pressure at ambient temperature.

15. The method of claim 14 wherein said ionic liquid is selected from the group of ionic liquids consisting of a cation,

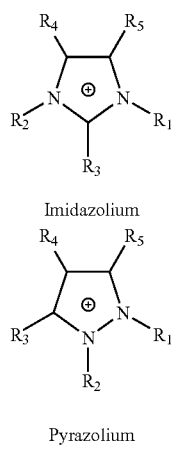

Imidazolium

Pyrazolium wherein $R_1$ and $R_2$ represent, independently, an alkyl group comprising 1 to 12 carbon atoms, and $R_3$, $R_4$, and $R_5$ represent either H, F, or separate alkyl groups of 1 to 5 carbon atoms, respectively, and said ionic liquid is selected from the group of ionic liquids consisting of an anion selected from the group consisting of $PF_6^-$, $BF_4^-$, $AsF_6^-$, triflate, imide, BETI, and imide ion of the type $(FX^1O)N^-(OX^2F)$ wherein $X^1$ and $X^2$ are the same or different and comprise SO or PF.

16. A method for detecting and identifying multiple volatile organic and/or volatile inorganic substances present in different vapors in an environment comprising the steps of:

a. providing a gas detector having a sensing means and a detecting means for detecting electrical capacitance variance of said sensing means and for further identifying said volatile organic and/or volatile inorganic substances, said sensing means comprising an array of sensing units wherein each sensing unit has a sensing material allocated therein, said sensing material being an ionic liquid which is exposed to said environment and is capable of dissolving a quantity of said volatile substance upon exposure thereto, said sensing means constituting an electrochemical capacitor and said each sensing unit in said array has an analyte-specific ionic liquid different from the other sensing units and each sensing unit having independent electrical communication with said detecting means, and said detecting means being in electrical communication with said sensing means, said each sensing unit further comprising an electrically nonconductive housing having said ionic liquid allocated therein and said housing having a recessed area or opening for allowing said ionic liquid to be exposed to said environment and is capable of dissolving a quantity of said volatile substance upon exposure thereto, said each sensing unit further comprising a plurality of electrodes within close proximity of one another disposed within said housing, said plurality of electrodes in electrical communication with said ionic liquid and said plurality of electrodes further being coated with said ionic liquid, said detecting means comprising at least one capacitance detection circuit in electrical communication with said sensing unit and a means to analyze and display data obtained by said capacitance detection circuit;

b. placing said gas detector in said environment that is to be analyzed; and c. exposing said ionic liquid in each of said sensing units to said environment for a sufficient time to allow said quantity of said volatile substance to dissolve in said ionic liquid and to allow said ionic liquid to adsorb onto the surface of said electrodes, thereby altering the capacitance of said electrochemical capacitor wherein said ionic liquid is an electrolyte.

17. The method of claim 16 further comprising the step of measuring said capacitance variance of said sensing means.

18. The method of claim 17 further comprising the step of identifying said volatile substance present in said environment.

19. The method of claim 16 wherein said electrodes are comprised of electrically conductive material selected from the group consisting of activated carbon, carbon nanotubes, buckyballs and porous metal oxides.

20. The method of claim 16 wherein said ionic liquid has a zero vapor pressure at ambient temperature.

* * * * *